US011682145B2

United States Patent
Zeller

(10) Patent No.: US 11,682,145 B2
(45) Date of Patent: Jun. 20, 2023

(54) SYSTEMS AND METHODS FOR GENERATING MEDICAL IMAGE DATA FOR LONGITUDINAL STUDIES

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 228 days.

(21) Appl. No.: 17/127,155

(22) Filed: Dec. 18, 2020

(65) Prior Publication Data

US 2021/0192801 A1    Jun. 24, 2021

(30) Foreign Application Priority Data

Dec. 20, 2019    (DE) .......................... 102019220456.2

(51) Int. Cl.
*G06T 11/00*    (2006.01)
*G06T 3/40*    (2006.01)
(Continued)

(52) U.S. Cl.
CPC ............ *G06T 11/00* (2013.01); *G06T 3/4046* (2013.01); *G06T 3/4053* (2013.01); *G06T 5/009* (2013.01);
(Continued)

(58) Field of Classification Search
CPC ..... G06T 11/00; G06T 3/4053; G06T 3/4046; G06T 5/009; G06T 7/0012;
(Continued)

(56) References Cited

U.S. PATENT DOCUMENTS 8,249,309 B2 *    8/2012  Kurzweil ............. G06V 10/993
                                                              382/176
11,067,653 B2 *   7/2021  Beck ................... G01R 33/4826
(Continued)

FOREIGN PATENT DOCUMENTS

WO    WO-2015159172 A1 * 10/2015 ............. A61B 5/055
WO    WO-2019103912 A2 *  5/2019 ............... G06N 3/08
WO    WO-2021146699 A1 *  7/2021

OTHER PUBLICATIONS

Guibas, John T., Tejpal S. Virdi, and Peter S. Li. "Synthetic medical images from dual generative adversarial networks." arXiv preprint arXiv: 1709.01872 (2017).*
(Continued)

*Primary Examiner* — Shefali D Goradia
(74) *Attorney, Agent, or Firm* — Banner & Witcoff Ltd.

(57) ABSTRACT

In a method for generating synthetic medical image data, first image data of an object under examination including a first value for a property is acquired, second image data of the object under examination including a second value for the property is acquired, the second value of the property of the second image data is matched to the first value to modify the second image data to generate synthetic image data, and the synthetic image data is provided (e.g. in electronic form as a data file). The first image data can be captured with a first magnetic resonance device at a first point in time, and the second image data can be captured with a second magnetic resonance device at a second point in time.

18 Claims, 4 Drawing Sheets

(51) Int. Cl.
  *G06T 5/00* (2006.01)
  *G06T 7/00* (2017.01)
  *G16H 30/40* (2018.01)
  *G16H 50/20* (2018.01)
  *G16H 30/20* (2018.01)

(52) U.S. Cl.
  CPC ............ *G06T 7/0012* (2013.01); *G16H 30/20* (2018.01); *G16H 30/40* (2018.01); *G16H 50/20* (2018.01); *G06T 2207/10088* (2013.01); *G06T 2207/20081* (2013.01); *G06T 2207/20084* (2013.01); *G06T 2210/41* (2013.01)

(58) Field of Classification Search
  CPC . G06T 2207/20084; G06T 2207/20081; G06T 2207/10088; G06T 2210/41; G16H 50/20; G16H 30/40; G16H 30/20
  See application file for complete search history.

(56) References Cited

U.S. PATENT DOCUMENTS

| | | | | |
|---|---|---|---|---|
| 11,151,690 | B2* | 10/2021 | Jia | G06T 7/90 |
| 2017/0311844 | A1* | 11/2017 | Zhao | A61B 1/009 |
| 2019/0370608 | A1* | 12/2019 | Lee | G06N 3/084 |
| 2021/0142116 | A1* | 5/2021 | Jaipuria | G06N 3/08 |

OTHER PUBLICATIONS

Dong et al., "Learning a Deep Convolutional Network for Image Super-Resolution," European Conference on Computer Vision. Springer, Cham, 2014.

Pham, Chi-Hieu, "Deep learning for medical image super resolution and segmentation," Dissertation, 2018.

Dar et al., "Image Synthesis in Multicontrast MRI with Conditional Generative Adversarial Networks," IEEE Transactions on Medical Imaging (2018).

Lavini et al., "Do different MRI scanners produce different fMRI results?," Proc. Intl. Soc. Mag. Reson. Med., vol. 9, pp. 1236 (2001).

Tax et al., "Cross-scanner and cross-protocol diffusion MRI data harmonisation: A benchmark database and evaluation of algorithms," NeuroImage, vol. 195, pp. 285-299 (2019).

EP Search Report for German Application No. 10 2019 220 456.2, dated Sep. 21, 2020.

* cited by examiner

SYSTEMS AND METHODS FOR GENERATING MEDICAL IMAGE DATA FOR LONGITUDINAL STUDIES

CROSS REFERENCE TO RELATED APPLICATIONS

This patent application claims priority to German Patent Application No. 10 2019 220 456.2, filed Dec. 20, 2019, which is incorporated herein by reference in its entirety.

BACKGROUND

Field

The disclosure relates to a method, an image processor, a computer program product and an electronically readable data storage medium for generating synthetic medical image data.

Related Art

In a magnetic resonance device, the body to be examined of an object under examination, in particular of a patient, is conventionally exposed to a relatively high main magnetic field, for example of 1.5 or 3 or 7 tesla, with the assistance of a main magnet. In addition, gradient pulses are played out with the assistance of a gradient coil unit. High-frequency radio-frequency pulses, for example excitation pulses, are then emitted via a radio-frequency antenna unit by means of suitable antenna facilities which results in the nuclear spins of specific atoms resonantly excited by these radio-frequency pulses being tilted by a defined flip angle relative to the magnetic field lines of the main magnetic field. On relaxation of the nuclear spins, radio-frequency signals known as magnetic resonance signals are emitted which are received by suitable radio-frequency antennas and then further processed. Finally, the desired image data can be reconstructed from the raw data acquired in this manner. Image data typically depicts an examination region, in particular a sub-region of the object under examination, in two or three dimensions. Image data typically has a spatial resolution of between 0.2 mm and 20 mm.

Examinations by means of magnetic resonance devices for producing medical image data of an object under examination are typically costly and time-consuming and can only be carried out in radiological clinics and/or hospitals. Depending on the clinical situation or diagnosis, there is a need to capture medical image data from an object under examination, in particular a patient, not just once but repeatedly over the course of a disease and/or in the context of therapeutic treatment. The periodicity and frequency of examinations and medical image data captures varies individually. Repeated captures of medical image data may generally be referred to as a study.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
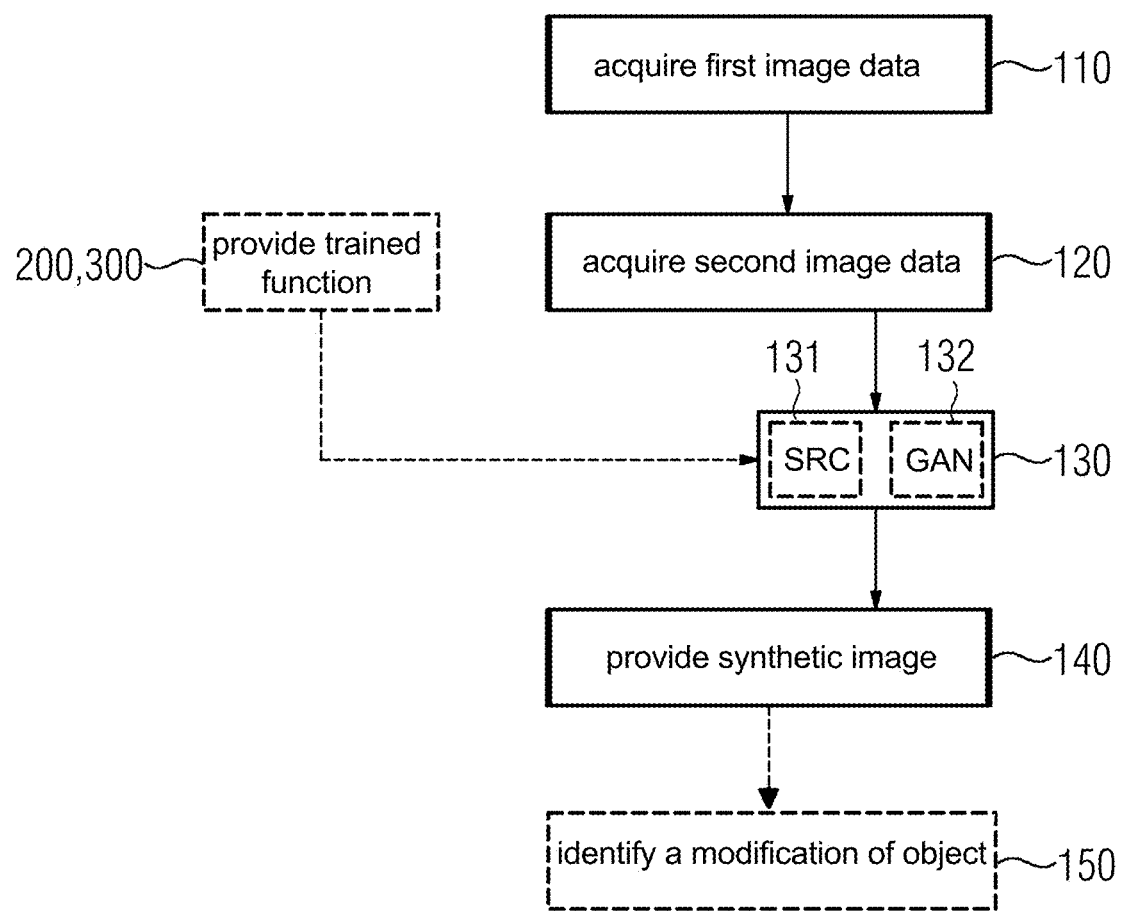
FIG. 1 shows a flowchart of a method for generating synthetic medical image data according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a particularly simple and inexpensive method for generating synthetic image data for longitudinal studies.

In an exemplary embodiment, the method according to the disclosure for generating synthetic medical image data provides the following method steps:

acquisition of first image data of an object under examination including a first value for a property and captured with a first magnetic resonance device at a first point in time, acquisition of second image data of the object under examination including a second value for the property and captured with a second magnetic resonance device at a second point in time, modification of the second image data comprising matching the property of the second image data to the first value, wherein synthetic image data is generated, provision of the synthetic image data.

The first image data is typically acquired by provision of the first image data by a memory unit on which the first image data is stored. In an exemplary embodiment, the first image data was captured at a past first point in time with the assistance of the first magnetic resonance device. The property of the first image data includes the first value.

The second image data is typically acquired by provision of the second image data by a memory unit on which the second image data is stored. The second image data may have been captured at a past second point in time with the assistance of the second magnetic resonance device. The property of the second image data includes the second value. Acquisition of the second image data may also comprise capture of the second image data of the object under examination at the second point in time with the second magnetic resonance device. Acquisition of the second image data may in particular comprise acquisition of the raw data and/or reconstruction of the raw data to yield second image data. The method according to the disclosure may accordingly be carried out at least in part at the second point in time. The first image data may also include a plurality of first values which are present in spatially resolved and/or voxel-by-voxel form and/or apply to one or more tissue types.

The second image data may also include a plurality of second values which are present in spatially resolved and/or voxel-by-voxel form and/or apply to one or more tissue types.

The first image data and the second image data image the same object under examination. There is an at least partial overlap of the examination region imaged in the first image data and in the second image data. The first magnetic resonance device typically differs from the second magnetic resonance device. The first magnetic resonance device may correspond to the second magnetic resonance device. In an exemplary embodiment, if the first magnetic resonance device corresponds to the second magnetic resonance device, the first acquisition method used for capturing the first image data differs from a second acquisition method used for capturing the second image data. The second acquisition method may, for example, comprise capture of less raw data than the first acquisition method.

The first value and the second value typically differ from one another. The first value is typically characteristic of the property and the first magnetic resonance device. The first value may be characteristic of an acquisition method used on the first magnetic resonance device. The second value is typically characteristic of the property and the second magnetic resonance device. The second value may be characteristic of an acquisition method used on the second magnetic resonance device. In an exemplary embodiment, the acquisition methods used for capturing the first image data on the first magnetic resonance device and for capturing the second image data on the second magnetic resonance device largely correspond to one another. For example, a T1-weighted TSE sequence was in each case used for capturing the first image data on the first magnetic resonance device and for capturing the second image data on the second magnetic resonance device. An acquisition method is typically characterized by the magnetic resonance-control sequence and/or the contrast of the image data.

The property may for example be a spatial resolution and/or a signal-to-noise ratio (SNR) and/or a contrast-to-noise ratio (CNR) and/or a contrast. The property may also comprise a plurality of the stated examples, wherein one example may be considered to be a sub-property of the property. In an exemplary embodiment, the first image data and the second image data each include a value for each sub-property, i.e. a first value and a second value per sub-property. In an exemplary embodiment, provision of the synthetic image data also comprises provision of the first image data.

The second image data is typically modified in such a manner that the property of the synthetic image data assumes a value characteristic of the first image data. Matching the property of the second image data to the first value may also be denoted approximation and/or adaptation and/or adjustment. Matching may for example be carried out by interpolation and/or by statistical means. The synthetic image data is accordingly based on the second image data, but includes at least the property of the first image data which is changed in the course of modification. In an exemplary embodiment, matching proceeds in such a manner that the visual appearance of the second image data matches the visual appearance of the first image data. In an exemplary embodiment, one difference between the first image data and the synthetic image data is typically the different point in time of the acquisition thereof and only this chronological difference. The first image data and the second image data may also at least in part image different examination regions. Modification of the second image data may also comprise an inverse reconstruction of the second image data matched to the first value In particular, the synthetic image data may then in particular be present as raw data.

This enables high consistency between the synthetic image data and the first image data, in particular with regard to the property. This enables good comparability of the synthetic image data with the first image data when different magnetic resonance devices are used for generating the first image data and the second image data. As a consequence, different magnetic resonance devices may be used over the course of a longitudinal investigation, wherein any resultant difference which is visually apparent and/or discernible for an automatic evaluation is suppressed according to the inventive method. In particular, the quality of the synthetic image data is matched to the quality of the first image data. The method according to the disclosure enables robust analysis of the first image data in comparison with the synthetic image data. The method according to the disclosure likewise enables a diagnosis on the basis of the synthetic image data which have the quality of the first image data. As a consequence, the method according to the disclosure enables simple and inexpensive generation of synthetic image data for longitudinal studies. The object under examination and/or the radiologist is thus relieved of the burden of having to select a specific magnetic resonance device, so improving flexibility.

One embodiment of the method provides that the property comprises a spatial resolution and a contrast, the first value comprises a first resolution value and a first contrast value and the second value comprises a second resolution value and a second contrast value. The first value may also comprise two or more contrast values. The second value may also comprise two or more contrast values. Spatial resolution is a measure which is the inverse of the size of the image data voxels. Contrast, in particular the contrast value, is a measure of a difference in signal intensity in the image data between two tissue types. Contrast, in particular a contrast value, is accordingly dependent on in each case two different tissue types, both of which are depicted in the image data. Contrast is typically dependent on the acquisition method and magnetic resonance device used, in particular also on the strength of the main magnetic field thereof. Even in the case of the same resolution and same acquisition method, two identical tissue types typically have a different contrast in the first image data and in the second image data. The first value typically comprises at least one first contrast value which is dependent on two tissue types. In an exemplary embodiment, the first value comprises two or more first contrast values, wherein in each case a first contrast value is dependent on in each case two tissue types. The second value typically comprises at least one second contrast value which is dependent on two tissue types. In an exemplary embodiment, the second value comprises two or more first contrast values, wherein in each case a second contrast value is dependent on in each case two tissue types.

According to this embodiment of the method, the property comprises two sub-properties, each of which may also in itself be a property in the method according to the disclosure. In particular the contrast and spatial resolution of image data may be highly dependent on the magnetic resonance device used and accordingly differ between the first image data and the second image data, even if the same acquisition method was selected during the captures of the first image data and the second image data. This embodiment accordingly ensures that the typically strongest properties which influence visual perception are matched and enables a robust analysis of the first image data in comparison with the synthetic image data. The method according to the disclosure likewise enables a diagnosis on the basis of the synthetic image data which, at least with regard to resolution and contrast, have the quality of the first image data.

An exemplary embodiment of the method provides that the first point in time and the second point in time differ by at least one day. The first point in time and the second point in time typically differ by at least one week, preferably by at least one month and particularly preferably by at least six months. The first point in time and the second point in time may also differ by more than one year. This embodiment enables consistent follow-up examinations which in particular require second image data in order to observe the progress of a disease and/or therapeutic treatment.

One embodiment of the method provides the additional method steps:
  acquisition of third image data of the object under examination including a third value for the property and captured with a third magnetic resonance device at a third point in time,
  modification of the third image data comprising matching the property of the third image data to the first value, wherein third synthetic image data is generated.

The method may optionally comprise these further method steps:
  acquisition of fourth image data of the object under examination including a fourth value for the property and captured with a fourth magnetic resonance device at a fourth point in time,
  modification of the fourth image data comprising matching the property of the fourth image data to the first value, wherein fourth synthetic image data is generated.

The third point in time is typically chronologically after the second point in time. The fourth point in time is typically chronologically after the third point in time. This embodiment accordingly enables repeated and long-term observation of a disease and/or therapeutic treatment.

One embodiment of the method provides that the first magnetic resonance device and the second magnetic resonance device have main magnetic fields which differ in strength from one another. The first magnetic resonance device or the second magnetic resonance device may for example take the form of a stationary magnetic resonance device permanently installed in a radiological clinic and/or hospital. A stationary magnetic resonance device may for example be characterized by a, typically permanent, arrangement in an RF-shielded room and/or by a main magnetic field of at least 0.5 tesla, in particular of at least 1.0 tesla. A stationary magnetic resonance device may be characterized in that the patient accommodation zone has a sufficiently large opening for a patient to be completely examined at least in portions.

The first magnetic resonance device or the second magnetic resonance device may for example take the form of a mobile magnetic resonance device. A mobile magnetic resonance device typically has a main magnetic field of less than 1.0 tesla, preferably of less than 0.5 tesla. A mobile magnetic resonance device may for example take the form of a "point-of-care" magnetic resonance device. A mobile magnetic resonance device may be specifically configured for an examination region, such as for example an extremity and/or a joint, for example the shoulder, and/or the head. In particular, a mobile magnetic resonance device may preferably be operated independently of an RF-shielded room.

In an exemplary embodiment, the first magnetic resonance device is a stationary magnetic resonance device. In an exemplary embodiment, the second magnetic resonance device is a mobile magnetic resonance device and/or the second magnetic resonance device has a smaller main magnetic field than the first magnetic resonance device. The SNR and/or CNR and/or spatial resolution typically increase with increasing main magnetic field strength. In particular, given the same examination time, a magnetic resonance device with a lower main magnetic field can only achieve an SNR at a lower spatial resolution than a magnetic resonance device with a stronger main magnetic field.

This embodiment enables good comparability between the first image data and the second image data despite different main magnetic field strengths. In particular, even if the second main magnetic field is smaller than the first main magnetic field, synthetic image data with comparable quality to the first image data is generated.

One embodiment of the method provides that the property is a spatial resolution and/or an SNR and/or a CNR and the first value is greater than the second value. If the first magnetic resonance device has a stronger main magnetic field than the second magnetic resonance device, the property comprises at least one spatial resolution, the second point in time is after the first point in time and the first value is greater than the second value, this embodiment enables the generation of high-resolution synthetic image data, in particular with the first value. The first magnetic resonance device is typically a stationary magnetic resonance device and the second magnetic resonance device a mobile magnetic resonance device. As a consequence, high-resolution synthetic image data can be generated on the basis of second image data captured with a simple, for example mobile, magnetic resonance device. If the property additionally comprises a contrast, even this can be adapted to the contrast of a stationary magnetic resonance device. As a consequence, follow-up examinations can be carried out on less costly magnetic resonance devices, whereby the total costs and/or quality of a therapeutic treatment can be improved. Patient satisfaction may likewise be increased since mobile magnetic resonance devices can also be installed in less densely populated regions, with costs nevertheless being covered, so shortening patients' journeys for follow-up examinations. Mobile magnetic resonance devices are often less frequently considered claustrophobic.

One embodiment of the method provides that the property is a spatial resolution and/or an SNR and/or a CNR and the first value is less than the second value. According to this embodiment, the first magnetic resonance device has a smaller main magnetic field than the second magnetic resonance device and the second point in time is before the first point in time. According to this embodiment, the second image data captured chronologically first is matched to the subsequently captured first image data which is typically of lower spatial resolution. As a consequence, the higher spatial resolution of the original second image data with a lower spatial resolution is adapted to the more recent first image data.

This is in particular advantageous in the case of an automatic evaluation of the first image data and the synthetic image data, in particular by a convolutional neural network. The first image data and/or the synthetic image data are here typically not visually analyzed and artifacts can be avoided due to the increase in resolution and/or the time required for automatic evaluation of the first image data and the synthetic image data can be reduced.

One embodiment of the method provides an additional method step of identifying a modification of the object under examination by comparison of the synthetic image data with the first image data.

In an exemplary embodiment, the comparison of the synthetic image data with the first image data proceeds at least partially automatically. The comparison enables the identification of a modification within the examination region which has occurred between the first point in time and the second point in time. Identification may be on the basis of visual and/or sub-visual features. Due to the matched quality of the synthetic image data and the first image data, despite the different magnetic resonance devices, the comparison is particularly effective and the identification of small modifications is enabled.

One embodiment of the method provides that the second image data is modified by using a trained function. The trained function may for example comprise a convolutional neural network and/or a super-resolution convolutional neural network and/or a generative adversarial network. It is known that trained functions in the form of neural networks can be used in the context of image processing. In particular the use thereof in longitudinal studies, on transfer of a property of first image data to second image data, wherein the first image data and the second image data predominantly differ only with regard to the property, is particularly advantageous. The first image data and the second image data predominantly differ only with regard to the property that said image data predominantly represents the same examination region of the same object under examination at two different points in time. A substantially smaller difference between the first image data and the second image data arises from physiological changes. As a consequence, the second image data can be particularly efficiently modified by using a trained function.

One embodiment of the method provides that the property comprises a spatial resolution, the first value comprises a first resolution value, the second value comprises a second resolution value, the trained function comprises a super-resolution convolutional neural network (SRCNN) and the modification of the second image data comprises matching the property of the second image data to the first resolution value by using the SRCNN. The use of an SRCNN in the field of medical image data for increasing resolution has already been published in Dong, Chao, et al. "Learning a deep convolutional network for image super-resolution." European Conference on Computer Vision. Springer, Cham, 2014, and Pham, Chi-Hieu. "Deep learning for medical image super resolution and segmentation." Diss. 2018, where the structure of such a neural network is also disclosed.

The SRCNN according to this embodiment is configured to increase a spatial resolution of source image data, in particular the second image data, during generation of the synthetic image data and to match the spatial resolution of the first image data. In particular during training of the SRCNN, which takes account of the property of spatial resolution in the first magnetic resonance device and in the second magnetic resonance device, in particular as a function of the acquisition method, the SRCNN is configured to generate synthetic image data with particularly high quality and the same resolution as the first image data. Spatial resolution in particular is an important property for consistency and/or comparison of image data. The method according to this embodiment is particularly robust.

One embodiment of the method provides that the property comprises a contrast, the first value comprises a first contrast value, the second value comprises a second contrast value, the trained function comprises a generative adversarial network (GAN) and the modification of the second image data comprises matching the property of the second image data to the first contrast value by using the generative adversarial network.

The use of a GAN in the field of medical image data for modifying a contrast has already been published in Dar, Salman U H, et al. "Image synthesis in multicontrast MRI with conditional generative adversarial networks." IEEE Transactions on Medical Imaging (2019), where the structure of such a GAN is also disclosed.

The GAN according to this embodiment is configured to match a contrast of source image data, in particular the second image data, to the contrast of the first image data during generation of the synthetic image data. In particular during training of the GAN, which takes account of the property of contrast in the first magnetic resonance device and in the second magnetic resonance device, in particular as a function of the acquisition method, the GAN is configured to generate synthetic image data with particularly high quality and the same contrast as the first image data. Contrast in particular is an important property for consistency and/or comparison of image data. The method according to this embodiment is particularly robust.

The GAN preferably takes the form of a progressive GAN (pGAN), if the first image data and the second image data are registered to one another. The GAN preferably takes the form of a conditional GAN (cGAN), if the first image data and the second image data are not registered to one another.

One embodiment of the method according to the disclosure provides that the property comprises a spatial resolution and a contrast, the first value comprises a first resolution value and a first contrast value, the second value comprises a second resolution value and a second contrast value, the second image data is modified by using a trained function and the trained function comprises an SRCNN and a GAN. This means that synthetic image data which is particularly highly consistent with the first image data can be particularly robustly generated in a manner which is individual to the first magnetic resonance device, the second magnetic resonance device and the acquisition method.

One embodiment of the method provides that the trained function has been provided in accordance with a method according to the disclosure for providing a trained function. A function trained in this manner is particularly robust and well suited to use in the method according to the disclosure.

The first method according to the disclosure for providing a trained function provides the following method steps:
  acquisition of first training image data of a test object including a first value for a property and captured with a first test magnetic resonance device at a first training point in time,
  acquisition of second training image data of the test object including a second value for the property and captured with a second test magnetic resonance device at a second training point in time, training of a function on the basis of the first training image data and the second training image data, output of the trained function.

This method provides that training image data of a test object, in particular of a patient and/or person, is generated on two different test magnetic resonance devices. In an exemplary embodiment, when the trained function is used in the context of generating synthetic image data, the first test magnetic resonance device is similar to the first magnetic resonance device and/or the second test magnetic resonance device is similar to second magnetic resonance device. Similarity may mean that the manufacturer and/or the strength of the main magnetic field and/or the model correspond. The first test magnetic resonance device and the second test magnetic resonance device typically differ with regard to the strength of the main magnetic field thereof. In an exemplary embodiment, the first test magnetic resonance device is a stationary magnetic resonance device and/or the second test magnetic resonance device is a mobile magnetic resonance device.

The first training image data is typically acquired by provision of the first training image data by a memory unit on which the first training image data is stored. The first training image data may have been captured at a past first training point in time with the assistance of the first test magnetic resonance device. The property of the first training image data includes the first value. Acquisition of the first training image data may also comprise capture of the first training image data of the test object at the first training point in time with the first test magnetic resonance device. Acquisition of the first training image data may in particular comprise acquisition of the raw data and/or reconstruction of the raw data to yield first training image data. The method according to the disclosure may accordingly be carried out at least in part at the first training point in time. The second training image data is typically acquired by provision of the second training image data by a memory unit on which the second training image data is stored. The second training image data may have been captured at a past second training point in time with the assistance of the second test magnetic resonance device. The property of the second training image data includes the second value. Acquisition of the second training image data may also comprise capture of the second training image data of the test object at the second training point in time with the second test magnetic resonance device. Acquisition of the second training image data may in particular comprise acquisition of the raw data and/or reconstruction of the raw data to yield second training image data. The method according to the disclosure may accordingly be carried out at least in part at the second training point in time. The first training image data may also include a plurality of first values which are present in spatially resolved and/or voxel-by-voxel form and/or apply to one or more tissue types.

The second training image data may also include a plurality of second values which are present in spatially resolved and/or voxel-by-voxel form and/or apply to one or more tissue types.

In an exemplary embodiment, the first training image data and the second training image data are and/or were captured with the same acquisition method and/or from the same test object. Acquisition of the first training image data and of the second training image data differs only with regard to the training point in time of the acquisition and the test magnetic resonance device used. In an exemplary embodiment, the first training point in time and the second training point in time are selected such that their difference has no influence on a difference between the first training image data and the second training image data. A difference between the first training image data and the second training image data typically predominantly results from the property. The first training image data and the second training image data are accordingly particularly well suited to generating a trained function with regard to the property for use in a method according to the disclosure for generating synthetic image data.

Training may for example proceed by means of transfer learning on the basis of individual data for the test object. Individual data of the test object may for example comprise the first training image data, the second training image data, the age and/or size and/or gender and/or weight and/or disease process and/or diagnosis and/or fitness of the test object. Training of the function may in this way be particularly comprehensive, whereby the trained function is particularly robust.

In an exemplary embodiment, the method for providing a trained function is carried out on a plurality of test objects, typically on at least 100, preferably at least 1000 and particularly preferably at least 5000 test objects. The process here typically proceeds iteratively such that, once the method according to the disclosure has been carried out on a first test object and a trained function has been output, this trained function is used as the function when carrying out the method according to the disclosure on a second test object. A GAN or a CNN, in particular a SRCNN, may initially be used as the function. The plurality of test objects means that the trained function can be generated particularly robustly.

One embodiment of the method provides that the first training point in time and the second training point in time differ by less than one month. In an exemplary embodiment, the first training point in time and the second training point in time typically differ by less than one week and preferably by less than three days. According to this embodiment, the first training image data and the second training image data predominantly differ with regard to the property. The first training image data and the second training image data are accordingly particularly well suited to generating a trained function with regard to the property for use in a method according to the disclosure for generating synthetic image data. This enables particularly robust training of the function with regard to the property.

One embodiment of the method provides that the property comprises a resolution and the function comprises a super-resolution convolutional neural network. The functioning and advantages of an SRCNN for matching a resolution in image data have already been described in the context of the use of an SRCNN in the generation of synthetic image data. Features, advantages or alternative embodiments mentioned here may also be transferred to the embodiment of the method for providing a trained function and vice versa.

One embodiment of the method provides that the property comprises a contrast and the function comprises a generative adversarial network. The functioning and advantages of a GAN for matching a contrast in image data have already been described in the context of the use of a GAN in the generation of synthetic image data. Features, advantages or alternative embodiments mentioned here may also be transferred to the embodiment of the method for providing a trained function and vice versa.

The second method according to the disclosure for generating a trained function provides the following method steps:

acquisition of first training image data of a test object including a first value for a primary property, a second value for a secondary property, wherein the first value for the primary property and the second value for the secondary property are characteristic of image data captured with a first test magnetic resonance device, acquisition of a third value for the primary property and a fourth value for the secondary property, wherein the third value for the primary property and the fourth value for the secondary property are characteristic of image data captured with a second test magnetic resonance device, modification of the first training image data comprising first matching of the primary property of the first training image data to the third value and second matching of the secondary property of the first training image data to the fourth value, wherein second training image data is generated, training of a function on the basis of the first training image data and the second training image data, output of the trained function.

The first training image data is typically acquired by provision of the first training image data by a memory unit on which the first training image data is stored. The first training image data may have been captured at a past training point in time with the assistance of the first test magnetic resonance device with a first acquisition method. The primary property of the first training image data includes the first value. The secondary property of the first training image data includes the second value. Acquisition of the first training image data may also comprise capture of the first training image data of the test object at the first training point in time with the first test magnetic resonance device and the first acquisition method. Acquisition of the first training image data may in particular comprise acquisition of the raw data and/or reconstruction of the raw data to yield first training image data. The first training image data may also include a plurality of first values and/or a plurality of second values which are present in spatially resolved and/or voxel-by-voxel form and/or apply to one or more tissue types.

The third value for the primary property and the fourth value for the secondary property are typically acquired by provision by a memory unit on which the first training image data is stored. Acquisition of the third value for the primary property and the fourth value for the secondary property may also comprise a calculation of the third value and the fourth value taking account of the first test magnetic resonance device, the second test magnetic resonance device and the first acquisition method. Calculation may be performed using a trained function, in particular a CNN and/or a GAN, in particular a cGAN and/or pGAN. A value for a property characteristic of image data captured with a test magnetic resonance device is typically dependent on the acquisition method used. The third value and fourth value are typically characteristic of image data captured with a second test magnetic resonance device and the first acquisition method. The second training image data may accordingly be generated on the basis of a CNN and/or GAN, in particular a cGAN and/or pGAN.

In an exemplary embodiment, the primary property comprises a contrast. First matching preferably proceeds on the basis of a GAN. In an exemplary embodiment, the secondary property comprises a spatial resolution. In an exemplary embodiment, second matching proceeds on the basis of a CNN. The second value is greater or less than the fourth value.

This embodiment enables the provision of a trained function on the basis of training image data captured with just one test magnetic resonance device. Capture of second training image data is not necessary, since the third value of relevance to the primary property and the fourth value of relevance to the secondary property may be acquired and/or calculated. The second training image data may likewise be individually generated for each test object. As a consequence, training image data from just one test magnetic resonance device are required for this embodiment, which simplifies the method. In particular, a larger number of test objects is then available, so training may proceed with a larger volume of first training image data and second training image data, whereby the trained function becomes more robust.

In this case too, in an exemplary embodiment, the method for providing a trained function is carried out on a plurality of test objects, typically on at least 100, preferably at least 1000 and particularly preferably at least 5000 test objects. The process here typically proceeds iteratively such that, once the method according to the disclosure has been carried out on a first test object and a trained function has been output, this trained function is used as the function when carrying out the method according to the disclosure on a second test object. A GAN or a CNN, in particular a SRCNN, may initially be used as the function. The plurality of test objects means that the trained function can be generated particularly robustly.

The disclosure is furthermore based on an image processor with an input interface, an output interface and a computer, wherein the computer is configured to carry out a method according to the disclosure for providing synthetic medical image data.

The computer may be provided via the input interface with first image data and/or second image data and/or a comparison algorithm for comparing the synthetic image data with the first image data and/or a trained function. Further functions, algorithms or parameters required in the method may be provided to the computer via the input interface. The synthetic image data and/or a modification of the object under examination and/or a result of a comparison of the synthetic image data with the first image data and/or further results of an embodiment of the method according to the disclosure may be provided via the output interface. The computer may be integrated into the first magnetic resonance device and/or into the second magnetic resonance device. The computer may also be installed separately from the first magnetic resonance device and/or the second magnetic resonance device. The computer may be connected to the first magnetic resonance device and/or the second magnetic resonance device.

Embodiments of the image processor according to the disclosure are configured similarly to the embodiments of the method according to the disclosure for generating synthetic medical image data. The image processor may have further control components which are necessary and/or advantageous for carrying out a method according to the disclosure. The image processor may also be configured to transmit control signals and/or to receive and/or process control signals, so as to carry out a method according to the disclosure for generating synthetic medical image data. In an exemplary embodiment, the computer comprises a memory unit, on which computer programs and further software may be stored, by means of which a processor comprised by the computer automatically controls and/or carries out a method sequence of a method according to the disclosure.

A computer program product according to the disclosure may be loaded directly in a memory unit of a programmable computer and has program code means for carrying out a method according to the disclosure when the computer program product is run in the optimization unit. As a consequence, the method according to the disclosure can be carried out in a quick, identically repeatable and robust manner. The computer program product is configured such that it can carry out the method steps according to the disclosure by means of the computer. The computer must here in each case comprise the prerequisites such as for example an appropriate working memory, an appropriate graphics card or an appropriate logic unit for it to be possible to carry out the respective method steps efficiently. The computer program product is for example stored on an electronically readable medium or saved to a network or server, from which it may be loaded into the processor of a local computer which may be directly connected to the first magnetic resonance device and/or second magnetic resonance device or may be configured as part of the first magnetic resonance device and/or second magnetic resonance device. Control information for the computer program product may furthermore be stored on an electronically readable data storage medium. The control information of the electronically readable data storage medium may be designed such that, when the data storage medium is used in a computer, it carries out a method according to the disclosure. Examples of electronically readable data storage media are a DVD, a magnetic tape or a USB stick on which electronically readable control information, in particular software, is stored. If this control information (software) is read from the data storage medium and stored in a controller and/or computer, all the embodiments according to the disclosure of the previously described method can be carried out.

The disclosure is furthermore based on an electronically readable data storage medium, on which a program is stored which is provided to carry out a method for generating synthetic medical image data.

The advantages of the image processor according to the disclosure, of the computer program product according to the disclosure and of the electronically readable data storage medium according to the disclosure correspond substantially to the advantages of the method according to the disclosure for generating synthetic medical image data. Features, advantages or alternative embodiments mentioned in this connection are likewise applicable to the other embodiments and vice versa.

The disclosure is furthermore based on a training system with a first interface, a second interface and a training unit, wherein the training unit is configured to carry out a method according to the disclosure for providing a trained function.

The training unit may be provided via the first interface with first training image data and/or second training image data and/or a first value for a property and/or neural network, in particular a super-resolution convolutional neural network and/or a pGAN and/or cGAN. Further functions, algorithms or parameters required in the method may be provided to the training unit via the first interface. The trained function and/or further results of an embodiment of the method according to the disclosure for providing a trained function may be provided via the second interface. The training unit may be integrated into the first test magnetic resonance device and/or into the second test magnetic resonance device. The training unit may also be installed separately from the first test magnetic resonance device and/or the second test magnetic resonance device. The training unit may be connected to the first test magnetic resonance device and/or the second test magnetic resonance device.

Embodiments of the image processor according to the disclosure are configured similarly to the embodiments of the method according to the disclosure for providing a trained function. The image processor may have further control components which are necessary and/or advantageous for carrying out a method according to the disclosure. The image processor may also be configured to transmit control signals and/or to receive and/or process control signals, so as to carry out a method according to the disclosure for providing a trained function.

In an exemplary embodiment, the training unit comprises a memory unit, on which computer programs and further software may be stored, by means of which a processor comprised by the training unit automatically controls and/or carries out a method sequence of a method according to the disclosure.

A computer program product according to the disclosure may be loaded directly in a memory unit of a programmable training unit and has program code means for carrying out a method according to the disclosure when the computer program product is run in the training unit. As a consequence, the method according to the disclosure can be carried out in a quick, identically repeatable and robust manner. The computer program product is configured such that it can carry out the method steps according to the disclosure by means of the training unit. The training unit must here in each case comprise the prerequisites such as for example an appropriate working memory, an appropriate graphics card or an appropriate logic unit for it to be possible to carry out the respective method steps efficiently. The computer program product is for example stored on an electronically readable medium or saved to a network or server, from which it may be loaded into the processor of a local training unit which may be directly connected to the first test magnetic resonance device and/or second test magnetic resonance device or may be configured as part of a test magnetic resonance device. Control information for the computer program product may furthermore be stored on an electronically readable data storage medium. The control information of the electronically readable data storage medium may be designed such that, when the data storage medium is used in a training unit, it carries out a method according to the disclosure. Examples of electronically readable data storage media are a DVD, a magnetic tape or a USB stick on which electronically readable control information, in particular software, is stored. If this control information (software) is read from the data storage medium and stored in a controller and/or training unit, all the embodiments according to the disclosure of the previously described methods can be carried out.

The disclosure is furthermore based on an electronically readable data storage medium, on which a program is stored which is provided to carry out a method for providing a trained function.

The advantages of the training system according to the disclosure, of the computer program product according to the disclosure and of the electronically readable data storage medium according to the disclosure correspond substantially to the advantages of the method according to the disclosure for providing a trained function which have previously been explained in detail. Features, advantages or alternative embodiments mentioned in this connection are likewise applicable to the other embodiments and vice versa.

FIG. 1 shows a sequence diagram of a first embodiment of a method according to the disclosure for generating synthetic medical image data. The method begins with the acquisition of first image data of an object under examination according to method step 110 and the acquisition of second image data of the object under examination according to method step 120. Method steps 110 and 120 may be carried out consecutively or at least in part simultaneously. Modification of the second image data comprising matching the property of the second image data to the first value, wherein synthetic image data is generated, proceeds in method step 130. The synthetic image data is then provided according to method step 140. In an exemplary embodiment, the method further includes identifying a modification of the object under examination (step 150) by comparison of the synthetic image data with the first image data.

Matching of the property of the second image data to the first value according to method step 130 may proceed on the basis of a trained function which may optionally be provided according to method step 200, 300. Matching of the property of the second image data to the first value according to method step 130 may proceed by using a trained function comprising a super-resolution convolutional neural network according to method step 131, if the property comprises a spatial resolution, the first value comprises a first resolution value and the second value comprises a second resolution value. Additionally and/or alternatively, matching of the property of the second image data to the first value according to method step 130 may proceed by using a trained function comprising a generative adversarial network according to method step 132, if the property comprises a contrast, the first value comprises a first contrast value and the second value comprises a second contrast value.

Figure 2:
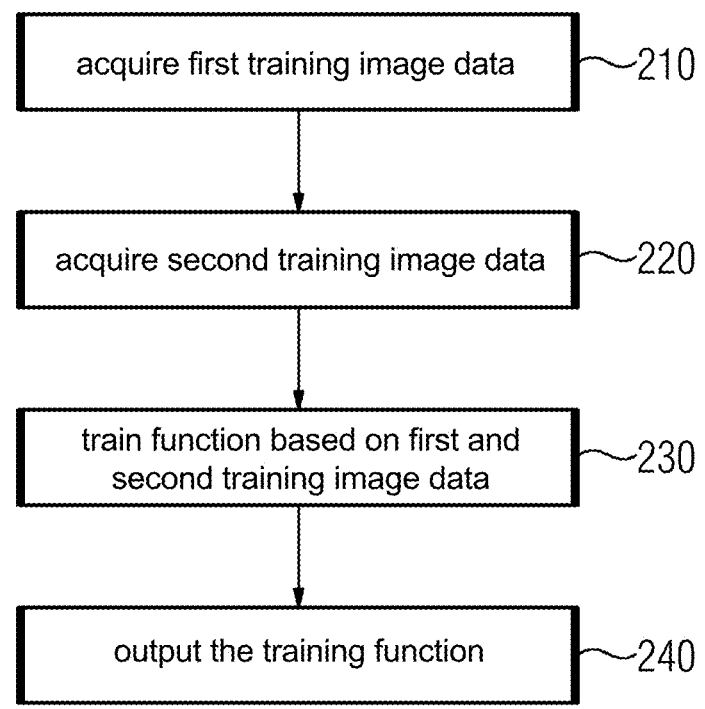
FIG. 2 shows a flowchart of a method for providing a trained function according to an exemplary embodiment.

FIG. 2 shows a sequence diagram of a first embodiment of a method 200 according to the disclosure for providing a trained function. According to said method 200, acquisition of first training image data of a test object including a first value for a property and captured with a first test magnetic resonance device at a first training point in time 81 proceeds in method step 210. Acquisition of second training image data of the test object including a second value for the property and captured with a second test magnetic resonance device at a second training point in time 82 proceeds in the following method step 220. Training of a function on the basis of the first training image data and the second training image data proceeds in method step 230. Output of the trained function proceeds in method step 240.

Figure 3:
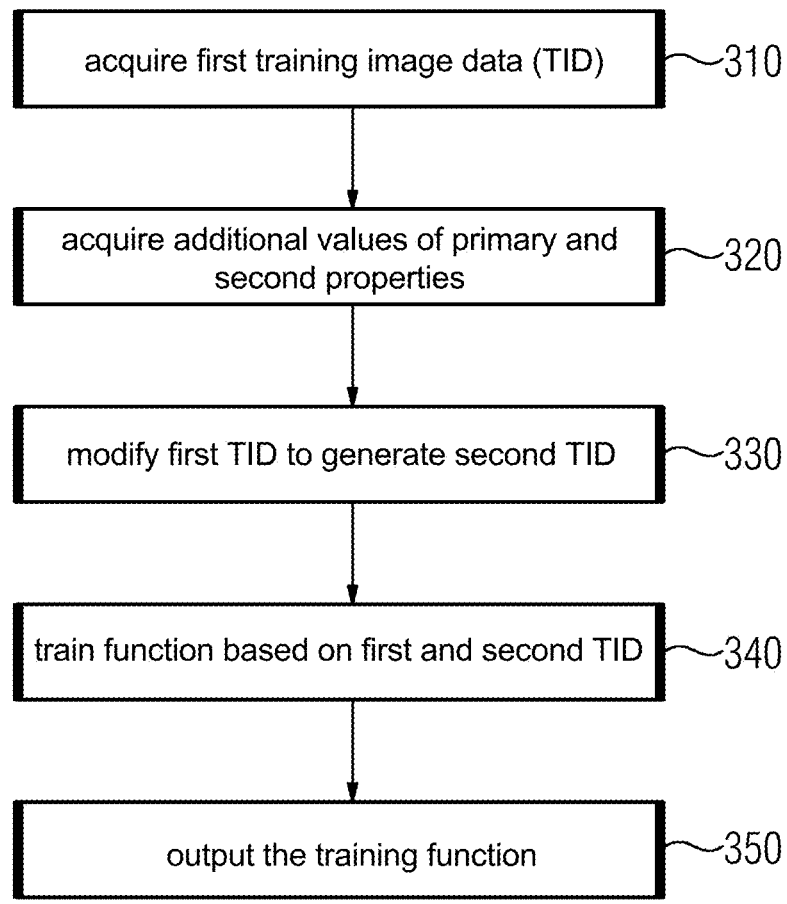
FIG. 3 shows a flowchart of a method for providing a trained function according to an exemplary embodiment.

FIG. 3 shows a sequence diagram of a second embodiment of a method according to the disclosure 300 for providing a trained function comprising a convolutional neural network and a generative adversarial network. The method 300 provides according to method step 310 acquisition of first training image data of a test object including a first value for a primary property, a second value for a secondary property, wherein the first value for the primary property and the second value for the secondary property are characteristic of image data captured with a first test magnetic resonance device. Acquisition of a third value for the primary property and a fourth value for the secondary property, wherein the third value for the primary property and the fourth value for the secondary property are characteristic of image data captured with a second test magnetic resonance device proceeds according to method step 320. Modification of the first training image data comprising first matching of the primary property of the first training image data to the third value and second matching of the secondary property of the first training image data to the fourth value, wherein second training image data is generated, proceeds according to method step 330. Training of a function on the basis of the first training image data and the second training image data then proceeds according to method step 340. The trained function is output in method step 350.

Figure 4:
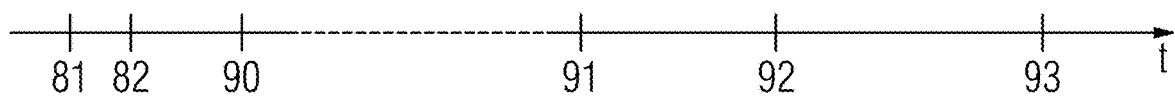
FIG. 4 shows a timeline visualizing points in time of relevance to the methods according to exemplary embodiments.

FIG. 4 shows a timeline visualizing the points in time in the method according to the disclosure which are of relevance to generating synthetic medical image data and providing a trained function. The method according to the disclosure for providing a trained function according to the second embodiment, as shown in FIG. 3, comprises the acquisition of first training image data, for example captured with a first test magnetic resonance device at a first training point in time 81. The first training point in time 81 and the second training point in time 82 are typically before the first point in time 91, the second point in time 92 and optionally the third point in time 93. The first training point in time 81 and the second training point in time 82 typically differ by less than one month and preferably by less than one week. The first point in time 91 and the second point in time 92 typically differ by at least one week and preferably by at least one month. The duration between the first point in time 91 and the first training point in time 81 is arbitrary, but a method 200 or 300 must be carried out at a further point in time 90, which is at least before the second point in time 92 and preferably also before the first point in time 91, if the method for generating synthetic medical image data proceeds by using a trained function.

Figure 5:
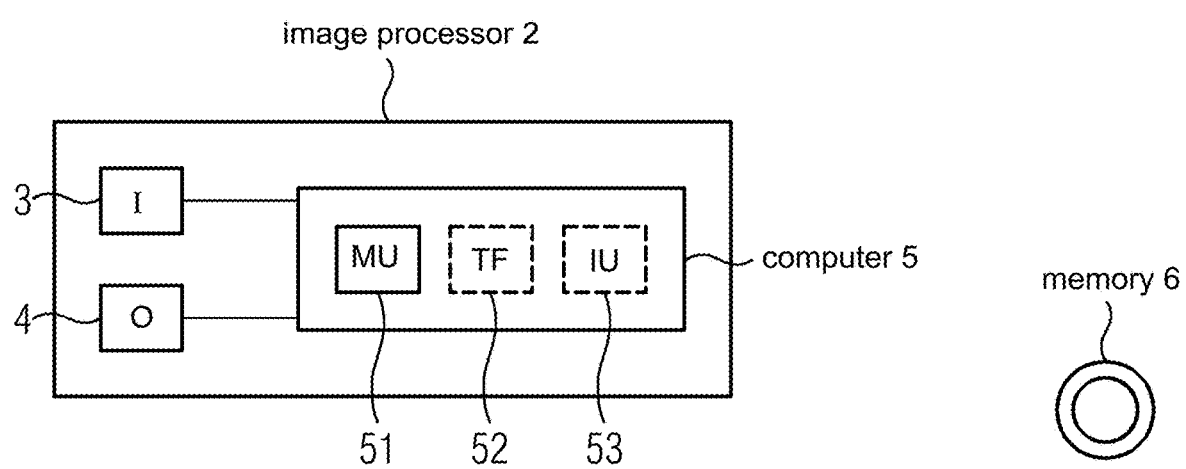
FIG. 5 shows a schematic diagram of an image processor according to an exemplary embodiment.

FIG. 5 shows a schematic diagram of an image processor 2 according to the disclosure. The image processor 2 comprises an input interface 3, an output interface 4 and a computer 5. In an exemplary embodiment, the image processor 2 (and/or one or more components therein) includes processor circuitry that is configured to perform one or more functions and/or operations of the image processor 2 (or respective component(s)).

The input interface 3 is configured to acquire first image data and/or second image data of an object under examination, i.e. to carry out method steps 110, 120. The output interface 4 is configured to provide the synthetic image data, i.e. to carry out method step 140. The computer 5 may comprise a modification unit (modifier) 51 and a trained function 52. The computer 5, in particular the modification unit 51, is configured to modify the second image data, wherein synthetic image data is generated. The second image data may be modified by using the trained function 52. The computer 5 may comprise an identification unit (identifier) 53 which is configured to identify a modification of the object under examination by comparison of the synthetic image data with the first image data. The image processor 2 together with the computer 5 is thus configured to generate synthetic medical image data, i.e. to carry out the method according to the disclosure.

In an exemplary embodiment, the computer 5 has computer programs and/or software which can be loaded directly into a memory unit, not described in any greater detail, of the computer 5, with program means for carrying out a method for generating synthetic medical image data when the computer programs and/or software are run in the computer 5. To this end, the computer 5 comprises a processor, not described in any greater detail, which is designed to run the computer programs and/or software. Alternatively, the computer programs and/or software may also be stored on an electronically readable data storage medium 31 configured separately from the image processor 2 and/or computer 5, wherein the computer 2 may access the data on the electronically readable data storage medium 31 via a data network.

A method for generating synthetic medical image data may also be present in the form of a computer program product which implements the method on the computer 5 when it is run on the computer 5. Likewise, an electronically readable data storage medium (memory) 6 with electronically readable control information stored thereon may be present, which control information comprises one such computer program product as has just been described and is designed to carry out the described method in a computer 5 of an image processor 2 using the data storage medium 6.

Although the disclosure has been illustrated and described in greater detail with reference to the preferred exemplary embodiments, the disclosure is not restricted by the disclosed examples and other variations may be derived therefrom by a person skilled in the art without going beyond the scope of protection of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for generating synthetic medical image data, comprising:
    acquiring first image data of an object under examination including a first value for a property, the first image data being captured with a first magnetic resonance device at a first point in time, wherein the property includes a spatial resolution and a contrast, the first value including a first resolution value and a first contrast value;
    acquiring second image data of the object under examination including a second value for the property, the second image data being captured with a second magnetic resonance device at a second point in time, wherein the second value includes a second resolution value and a second contrast value;
    modifying the second image data to generate synthetic image data, the modifying including matching the second value of the property of the second image data to the first value; and
    providing the synthetic image data in electronic form as a data file.

2. The method as claimed in claim 1, wherein the first point in time and the second point in time differ by at least one day.

3. The method as claimed in claim 1, wherein the first magnetic resonance device and the second magnetic resonance device have main magnetic fields which differ in strength from one another.

4. The method as claimed in claim 1, wherein:
the property further includes a signal-to-noise ratio (SNR) and/or a contrast-to-noise ratio (CNR); and
the first value is greater than the second value.

5. The method as claimed in claim 1, wherein:
the property further includes a signal-to-noise ratio (SNR) and/or a contrast-to-noise ratio (CNR); and
the first value is less than the second value.

6. The method as claimed in claim 1, further comprising comparing the synthetic image data with the first image data to identify a modification of the object under examination.

7. The method as claimed in claim 1, wherein the second image data is modified using a trained function.

8. The method as claimed in claim 7, wherein:
the trained function comprises a super-resolution convolutional neural network; and
the modification of the second image data comprises matching, using the super-resolution convolutional neural network, the second resolution value of the property of the second image data to the first resolution value by using the super-resolution convolutional neural network.

9. The method as claimed in claim 7, wherein:
the trained function comprises a generative adversarial network, and
the modification of the second image data comprises matching, using the generative adversarial network, the second contrast value of the property of the second image data to the first contrast value.

10. The method as claimed in claim 7, wherein the trained function is obtained by:
acquiring first training image data of a test object including a first value for a property, the first training image data being captured with a first test magnetic resonance device at a first training point in time;
acquiring second training image data of the test object including a second value for the property, the second training image data being captured with a second test magnetic resonance device at a second training point in time; and
training of a function based on the first training image data and the second training image data to obtain the trained function.

11. The method as claimed in claim 7, wherein the trained function is obtained by:
acquiring first training image data of a test object, the first training image data including a first value for a primary property and a second value for a secondary property, wherein the first value for the primary property and the second value for the secondary property are characteristic of image data captured with a first test magnetic resonance device;
acquiring a third value for the primary property and a fourth value for the secondary property, the third value for the primary property and the fourth value for the secondary property being characteristic of image data captured with a second test magnetic resonance device;
modifying the first training image data to generate second training data, the modifying including: a first matching of the primary property of the first training image data to the third value, and a second matching of the secondary property of the first training image data to the fourth value; and
training of a function based on the first training image data and the second training image data to obtain the trained function.

12. A computer program product, embodied on a non-transitory computer-readable storage medium, having a computer program and that is directly loadable into a memory of a programmable computer, when executed by a processor of the programmable computer, causes the processor to perform the method as claimed in claim 1.

13. A non-transitory computer-readable storage medium with an executable program stored thereon, that when executed, instructs a processor to perform the method of claim 1.

14. An image processing device comprising:
a communication interface; and
a processor configured to perform the method of claim 1 to generate the synthetic medical image data.

15. A method for generating synthetic medical image data, comprising:
acquiring first image data of an object under examination including a first value for a property, the first image data being captured with a first magnetic resonance device at a first point in time, wherein the property includes a spatial resolution and the first value includes a first resolution value;
acquiring second image data of the object under examination including a second value for the property, the second image data being captured with a second magnetic resonance device at a second point in time, wherein the second value includes a second resolution value;
modifying the second image data, using a trained function, to generate synthetic image data, the modifying including matching, using trained function, the second resolution value of the property of the second image data to the first resolution value; and
providing the synthetic image data in electronic form as a data file.

16. The method as claimed in claim 15, wherein trained function includes a super-resolution convolutional neural network, the matching using the super-resolution convolutional neural network.

17. A method for generating synthetic medical image data, comprising:
acquiring first image data of an object under examination including a first value for a property, the first image data being captured with a first magnetic resonance device at a first point in time, wherein the property includes a contrast, the first value including a first contrast value;
acquiring second image data of the object under examination including a second value for the property, the second image data being captured with a second magnetic resonance device at a second point in time, wherein the second value includes a second contrast value;
modifying the second image data, using a trained function, to generate synthetic image data, the modifying including matching, using the trained function, the second contrast value of the property of the second image data to the first contrast value; and
providing the synthetic image data in electronic form as a data file.

18. The method as claimed in claim 17, wherein trained function includes a generative adversarial network, the matching using generative adversarial network.

* * * * *